(12) United States Patent
Ogle et al.

(10) Patent No.: US 6,322,588 B1
(45) Date of Patent: Nov. 27, 2001

(54) MEDICAL DEVICES WITH METAL/POLYMER COMPOSITES

(75) Inventors: Matthew F. Ogle, St. Paul; Matthew S. Reimink, Little Canada; Richard F. Schroeder, Fridley, all of MN (US)

(73) Assignee: St. Jude Medical, Inc., St. Paul, MN (US)

(*) Notice: Subject to any disclaimer, the term of this patent is extended or adjusted under 35 U.S.C. 154(b) by 0 days.

(21) Appl. No.: 09/375,326

(22) Filed: Aug. 17, 1999

(51) Int. Cl.[7] .............................. A61F 2/02; A61L 29/00
(52) U.S. Cl. .................... 623/1.46; 623/23.58; 623/2.42; 427/2.3
(58) Field of Search .................. 623/23.58, 2.42, 623/1.46, 1.49, 2.3; 427/455, 456, 457; 428/205, 213; 604/265, 266

(56) References Cited

U.S. PATENT DOCUMENTS

| | | | |
|---|---|---|---|
| 4,743,493 | 5/1988 | Sioshansi et al. | 428/217 |
| 5,289,831 | 3/1994 | Bosley | 128/899 |
| 5,320,908 * | 6/1994 | Sodervall et al. | 428/461 |
| 5,368,608 * | 11/1994 | Levy et al. | 623/922 |
| 5,607,463 | 3/1997 | Schwartz et al. | 623/1 |
| 5,632,779 | 5/1997 | Davidson | 623/12 |
| 5,649,977 | 7/1997 | Campbell | 623/1 |
| 5,674,293 * | 10/1997 | Armini et al. | 606/76 |
| 5,713,949 | 2/1998 | Jayaraman | 623/1 |
| 5,716,400 | 2/1998 | Davidson | 623/2 |
| 5,725,573 | 3/1998 | Dearnaley et al. | 623/2 |
| 5,976,169 | 11/1999 | Imran . | |
| 5,984,905 * | 11/1999 | Dearnaley | 604/265 |

FOREIGN PATENT DOCUMENTS

| | | |
|---|---|---|
| 0 636 375 A1 | 2/1995 | (EP) . |
| WO 93 23092 | 11/1993 | (WO) . |
| WO 95/18637 | 9/1994 | (WO) . |
| WO 98/31404 | 1/1998 | (WO) . |
| WO 99/26666 | 11/1998 | (WO) . |
| WO 99/38544 | 1/1999 | (WO) . |
| WO 00/07633 | 2/2000 | (WO) . |
| WO 00/45724 | 8/2000 | (WO) . |

OTHER PUBLICATIONS

Pourrezaei et al., "Development of antimicrobial and anti-thrombogenic coatings for insede and outside of medical catheters," Slurface and Coatings Technology, 669–674, 1994.*

Cui et al., "Biomaterial modification by ion–beam processing," Surface and Coatings Technology, 278–285, 1999.*

* cited by examiner

Primary Examiner—Corrine McDermott
Assistant Examiner—Choon P. Koh
(74) Attorney, Agent, or Firm—Hallie A. Finucane; Patterson, Thuente, Skaar & Christensen, P.A.; Peter S. Dardi

(57) ABSTRACT

Medical devices are formed from metal/polymer composites that have improved characteristics. The metal/polymer composites have a relatively thick metal coating with an average metal thickness of greater than about 3 microns. The composite has mechanical properties, such as mechanical strength, durability and resiliency, contributed by the metal coating. The metal/polymer composites can be formed by solution based or vapor based approaches.

21 Claims, 2 Drawing Sheets

MEDICAL DEVICES WITH METAL/POLYMER COMPOSITES

BACKGROUND OF THE INVENTION

The invention relates to medical devices suitable for contacting a patient's bodily fluids, including a metal coated polymer substrate.

A variety of medical devices are designed particularly for contact with a patient's bodily fluids. The duration of this contact may be relatively short, as is typical with surgical instruments, or may be long term, as is typical with prosthetic heart valves implanted into the body of a recipient, and other implanted prostheses. Some articles such as catheters can have either short term or relatively long term contact.

Prostheses, i.e., prosthetic articles, are used to repair or replace damaged or diseased organs, tissues and other structures in humans and animals. Prostheses generally must be biocompatible since they are typically implanted for extended periods of time. Examples of prostheses include, without limitation, prosthetic hearts, prosthetic heart valves, ligament repair materials, vessel repair and replacement materials, stents, and surgical patches.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a mechanical or bioprosthetic, i.e., tissue based, valve. Another technique uses an annuloplasty ring to provide structural support to the natural annulus of the native valve.

Many biocompatible medical devices and/or their components have significant requirements with respect to their mechanical and physical properties. For example, the medical devices are often limited in their size. At the same time, the devices and/or their components may be subjected to demanding mechanical requirements, such as mechanical strength and long term wear requirements. Thus, there are significant restraints imposed on the design of many medical devices and/or their components.

As a particular example, heart valve stents are used to support tissue components within a bioprosthetic heart valve. Heart valve stents have been produced from polymers, such as polyacetals, for example Delrin® and Celcon®, or metals, such as titanium or a cobalt-chromium-nickel alloy, for example Elgiloy®. Polymer heart valve stents have been known to fail due to fatigue and creep. Furthermore, polymer heart valve stents need to be relatively bulky in order to withstand the repeated loading over the lifetime of the prosthetic valve.

In contrast, stents made from spring metals, such as Elgiloy®, exhibit better mechanical properties, such as strength and fatigue endurance, and can have a smaller cross-section than corresponding polymer stents. Metal heart valve stents, however, generally must be kept quite simple in geometry, and typically consist of a simple wire form. As the geometry of the metal stent becomes more complex, there is necessarily more metal joints, which can weaken the structure. Also, metal stents may require welding or crimping during their manufacture which can weaken the stent. These observations regarding properties and construction of heart valve stents can also apply to other medical devices and their components.

SUMMARY OF THE INVENTION

In a first aspect, the invention relates to a medical device comprising a substrate having a biocompatible metal coating over at least a portion of its surface with an average thickness greater than about 3 microns, wherein the substrate comprises a polymer.

In another aspect, the invention relates to a method of producing a medical device comprising applying a metal coating on a substrate, the metal coating having an average thickness greater than about 3 microns, wherein the substrate comprises a polymer.

DETAILED DESCRIPTION OF THE PREFERRED EMBODIMENTS

Figure 1:
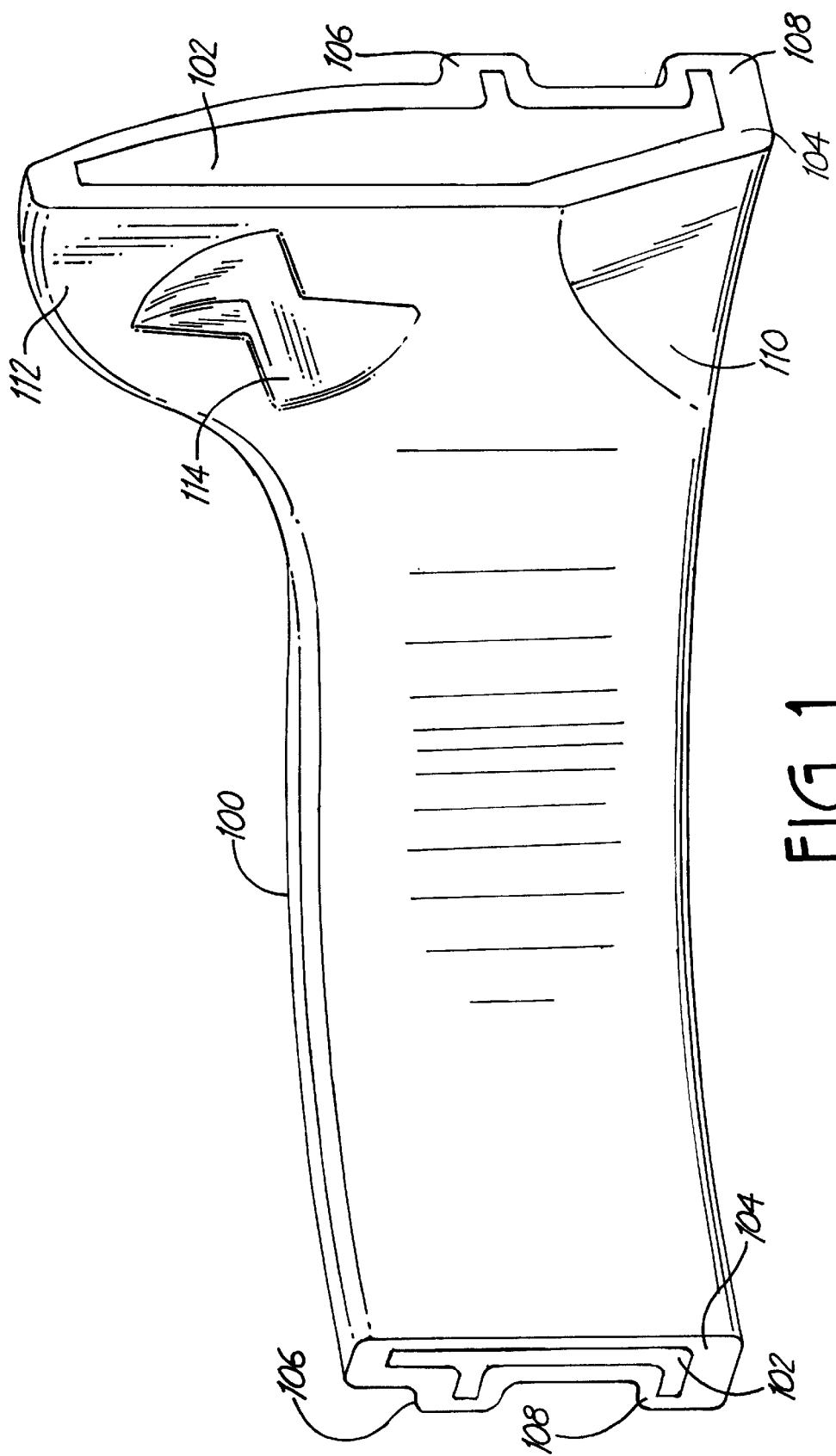
FIG. 1 is a fragmentary perspective view of a mechanical heart valve orifice.

Improved medical devices can be produced using metal/polymer composite materials described herein. In particular, the strength advantages of metal can be combined with the versatility of polymer components by applying a relatively thick metal coating over a polymer substrate. The metal coating preferably is thick enough such that the mechanical properties, such as mechanical strength, durability and resiliency, of the metal/polymer composite are significantly influenced by the metal. In addition, the metal/polymer composite is able to incorporate complex or other desired structural features in the polymer substrates. Thus, the metal/polymer composite combines advantages of both metal components and polymer components in a synergistic fashion to arrive at improved implantable components.

The polymer substrate for the metal/polymer composite generally includes many of the desired structural features of the composite, accounting for potential structural modification, if any, accompanying the application of the coating. In particular, the polymer substrate can be formed with a relatively complex geometry. The metal coating can cover all or a portion of the polymer substrate. If the polymer substrate is completely covered with metal, the polymer generally does not have to be biocompatible.

The metal coating preferably is applied at a sufficient thickness to provide the desired mechanical properties to the composite. Generally, at least a portion of the metal coating has a thickness normal to the polymer surface greater than about 3 microns. The metal coating can be applied uniformly over the substrate or a portion of the substrate, or the metal coating can be applied with variable properties, such as thickness, composition, texture and porosity, at different regions on the substrate. Generally, the metal imparts structural strength to the composite. In addition, metals with varying degrees of resiliency can be used to impart a desired degree of rigidity to the composite. For example, an especially resilient or memory metal, such as Nitinol®, a nickel-titanium alloy, can be used to provide a composite with particularly large resiliency.

In addition, application of the metal can provide for relatively minor alterations in the structure/geometry of the resulting composite in comparison with the structure/geometry of the underlying polymer substrate. For example, the deposition of the metal can cover small structural features in the substrate. Alternatively, selective deposition of the metal over the substrate can result in the formation of structure on the composite. Thus, the coating process can be used to adjust the geometric aspects of the composite without altering the geometry of the polymer substrate. The ability to make minor variations in the geometry of the composite without altering the mold of the polymer substrate can be a significant processing advantage.

Suitable approaches for the application of the metal coating may depend on the properties of the materials in the composite. In particular, the polymer substrate preferably is formed from a suitable polymer that can withstand, without undergoing drastic modification, the processing conditions used for the application of the metal coating. Preferred methods for the application of the metal coating include vapor deposition approaches and solution based approaches, as described further below.

In preferred embodiments, the metal coating is applied as a relatively thick coating, such that the mechanical properties of the composite are significantly determined by the metal coating. In particular, the metal coating preferably has an average thickness greater than about 3 microns. The application of a relatively thick metal coating to influence the mechanical properties of the composite can be distinguished from the application of thin metal coatings solely to influence the surface properties of the coated product without significantly influencing the mechanical properties.

Medical Devices

Relevant biocompatible articles include all medical devices that contact bodily fluids. These articles can be organized roughly into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a moist membrane, such as within a patient's mouth.

Implanted devices include, without limitation, prostheses such as pacemakers, electrical leads such as pacing leads, defibrillators, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledgets, suture, annuloplasty rings, stents, staples, valved grafts, dermal grafts for wound healing, orthopedic spinal implants, orthopedic pins, intrauterine devices (IUDs), urinary stents, maxial facial reconstruction plating, dental implants, intraocular lenses, clips, sternal wires, bone, skin, ligaments, tendons, and combinations thereof.

Percutaneous devices include, without limitation, catheters of various types, cannulas, drainage tubes such as chest tubes, surgical instruments such as forceps, retractors, needles, and gloves, and catheter cuffs. Catheters can be used for accessing various bodily systems such as the vascular system, the gastrointestinal tract, or the urinary system.

Cutaneous devices include, without limitation, burn dressings, wound dressings and dental hardware, such as bridge supports and bracing components. These biocompatible articles can be made from the biocompatible materials described below.

While the metal coated composites can be used in any of the medical devices described above, a few medical devices are of particular interest. Such devices of particular interest include, for example, heart valve prostheses, heart valve stents, heart valve leaflets, vascular stents, urinary stents, annuloplasty rings, mechanical heart valve components, pacemaker components, catheters, electrical leads, left ventricular assist devices, and orthopedic components.

Materials in the Metal/Polymer Composite

The metal/polymer composites include a polymer substrate and a metal coating. The substrate can include other materials such as metals and ceramics. Generally, at least a significant portion of the substrate to be covered with the metal coating is formed from one or more polymers. In preferred embodiments, the substrate is made only from one or more organic polymers.

Preferred metals for inclusion as a coating in the composite are biocompatible. In other words, the metals are suitable for contacting a patient's bodily fluids or tissue. One class of biocompatible metals are essentially inert and stable in contact with the patient's blood stream. Such inert metals include, for example, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol®, a nickel-titanium alloy.

Other metals can oxidize to dissolve at slow rates to provide a desirable biological response. For example, aluminum, manganese, iron and other metals can slowly form polyvalent metal ions ($Al^{+3}$, $Mn^{+2}$ and $Fe^{+3}$) that can inhibit calcification of implanted substrates in contact with a patient's bodily fluids or tissues. Use of anticalcific metals in medical devices generally is described further in copending and commonly assigned U.S. patent application Ser. No. 09/017,185, filed Feb. 2, 1998, entitled "CALCIFICATION-RESISTANT MEDICAL ARTICLES," incorporated herein by reference.

In addition, other metals, such as silver, gold, platinum, palladium, iridium, copper, tin, lead, antimony, bismuth and zinc, are known to have antimicrobial properties. Thus, composites can be formed from these antimicrobial metals to inhibit possible infection associated with the use of the medical device. The use of anticalcific metal in a medical device generally is described further in copending and commonly filed U.S. patent application Ser. No. 09/143,989, filed Aug. 31, 1998, entitled "Medical Article With Adhered Antimicrobial Metal," incorporated herein by reference.

Magnetizable coatings can be formed from suitable metals and alloys, such as cobalt, cobalt alloys and iron alloys. The magnetizable coating can be deposited in the presence of a magnetic field to orient the magnetic field of the coating, or it can be placed in a strong magnetic field to orient the magnetic field of the coating after it is formed. A magnetized coating can be used for magnetic therapy, as a magnetic marker, or for its interaction with an implantable electronic device.

Suitable polymers are stable with respect to the metal deposition process. Thus, the selection of a desirable polymer generally depends on the selection of the deposition process. Depending on the process being used to form the coating, one or more appropriate polymers can be used in the formation of the substrate. A polymer substrate can be fabricated from synthetic polymers as well as purified biological polymers. Appropriate synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly (epsilon-caprolactone), polylactic acid, polyglycolic acid, poly(dimethyl glycolic acid), poly(hydroxy butyrate), and similar copolymers.

Based on desirable properties and experience in the medical device field, preferred polymers include, for example, polyether ether ketones, acetals, polyamides (e.g., nylons), polyurethanes, polytetrafluoroethylene, polyester teraphthalate, polycarbonates, polysulfone, and resorbable polymers (e.g., polylactic acid and polyglycolic acid), and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable. Purified biological polymers can be appropriately formed into a polymer substrate.

The polymer substrates can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. Since significant mechanical strength is contributed by the metal coating, optimizing the mechanical strength of the polymer substrate may not be critical. The substrate can be textured or made porous by either physical abrasion or chemical alteration to facilitate incorporation of the metal coating.

An example of a preferred embodiment of a mechanical heart valve prosthesis formed from the composite materials described herein is shown in FIG. 1. In the fragmentary view of FIG. 1, heart valve prosthesis 100 includes a substrate 102, which is visible at the two fragmented ends. Substrate 102 is covered with a coating 104.

The substrate and corresponding coating include several elements of structure. First, the outer portion of the ring forming the prosthesis includes two rims 106, 108. Rims 106, 108 provide mechanical strength and stability, and generally may retain the rotation mechanism of a heart valve. The rim structure is formed in substrate 102 and built upon by coating 104. A contour 110 is located near the bottom of valve 100 to improve the hydrodynamic properties of valve 100. In addition, expanded portion 112 includes an opening 114 for a butterfly hinge. A description of butterfly hinges in the construction of a bileaflet mechanical heart valve is described further in copending and commonly assigned U.S. patent application Ser. No. 08/664,235 to Brendzel, entitled "Prosthetic Heart Valve With Increased Valve Lumen," incorporated herein by reference.

Figure 2:
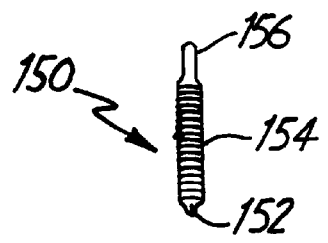
FIG. 2 is a side view of a dental implant with a metal coating of the invention.

FIG. 2 displays a dental implant 150. Dental implant 150 includes a pointed tip 152, a ringed body section 154, where the rings help to secure the implant, and top section 156 for securing a dental implement. In preferred embodiments, dental implant 150 includes a metal coating covering entirely a polymer substrate. The structure of tip 152 and top section 156 preferably is formed by contouring the substrate. The rings on body section 154 can be formed by selective deposition of the metal coating.

Figure 3:
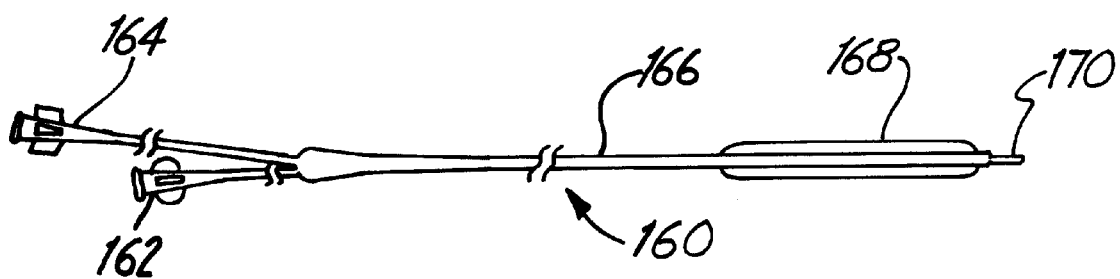
FIG. 3 is fragmentary, side view of a catheter.

Referring to FIG. 3, a catheter 160 is displayed. Catheter 160 includes proximal ends 162, 164, shaft 166, balloon 168 and a tip 170. If desired, tip 170 and or shaft 166 can be formed to include a metal coating, as described herein. If shaft 166 is coated with metal, the metal can be selected to provide mechanical strength without decreasing flexibility below desired values.

The metal coating thickness is measured along the normal (perpendicular) to the polymer substrate surface. If the metal penetrates the polymer surface such that the interface is not well defined, the thickness normal to the polymer surface is determined by an approximate average polymer thickness over a small but finite area of the polymer/metal interface. Measurement of metal thickness should not depend significantly on the exact approach of determining the normal to the polymer surface. For most applications, the average metal thickness generally is greater than about 3 microns, preferably greater than about 10 microns, more preferably from about 10 microns to about 1000 microns and even more preferably from about 10 microns to about 250 microns. For applications where greater mechanical strength is needed, such as in forming orthopedic devices, preferred thickness can be as large as about 5000 microns.

As noted above, all or a portion of the substrate can be covered with a metal coating. In some embodiments, the metal is applied in an approximately uniform coating over the relevant section or the entire surface of the substrate. In some preferred embodiments, a uniform coating is identifiable as a coating in which the thickness at all points along the substrate varies by less than about 20% and more preferably less than about 10% relative to the average coating thickness. Of course, if the metal coating does not cover the entire substrate, the edge of the coating forms an approximate discontinuity. The presence of an edge is not considered to contribute a non-uniform coating unless the slope at the edge extends over a macroscopically observable distance. In other words, a coating can be uniform over a portion of the substrate if the edges of the coating appear visibly sharp.

Alternatively, the metal can be applied in a non-uniform coating such that the thickness of the metal coating varies at different regions of the substrate. In some embodiments, it may be desirable for the maximum coating thickness to be more than a factor of 350 thicker relative to the minimum coating thickness or, alternatively, a factor of 10 or more larger than the average coating thickness. An intermediate range of coating thickness variation includes a coating that at all points varies by less than from about 25 percent to about 250 percent relative to the average coating thickness. Application of a non-uniform coating can accomplish a variety of goals including simplifying deposition, adding mechanical stability to stress points or locations and/or altering the geometry of the component/device. in particular, the metal coating can be thicker at portions of the substrate that are expected to be subject to high stress. Similarly, the thickness can be varied such that the mechanical properties more closely match the native structure. For example, the compliance of a stent or graft can be adjusted to match reasonably closely the properties of the native tissue since less compliance mismatch results in less turbulence and other performance anomalies.

Furthermore, the composition of the metal coating can have uniform composition or the composition can vary at different regions of the coating. For example, regions of particular stress can have a particular metal coating composition while other portions of the metal coating can be formed from other metals or combination of metals.

Similarly, the metal coating can have layers of metal with different compositions. Non-uniform and/or layered metal compositions can be introduced by either solution based or vapor based deposition approaches, as described further below. Texture can be incorporated onto the metal coating during deposition by masking the surface with a composition that can be later removed. The metal coating can be textured and/or made porous either by physical abrasion, chemical etching, electron bombardment or otherwise treating the surface following formation of the coating to promote desired host response.

Application of the Metal Coating

The metal coating is applied over all or a portion of a polymer substrate. Suitable approaches for applying the metal coating include vapor based approaches and solution based approaches. Preferred coating approaches include vapor deposition methods, such as sputtering and ion beam deposition. The coating process preferably forms an intimate connection between the substrate and the metal, such that the metal cannot be easily stripped from the substrate, if at all. In particular, in some embodiments, the metal penetrates into the surface of the polymer to form an intimate bond between the metal and the polymer.

The processes for applying the metal coating can be broadly classified as solution based approaches or vapor phase approaches. A combination of solution based approaches and vapor phase approaches can be used in forming a metal coating. Suitable solution based approaches include, for example, electrochemical deposition (i.e., electroplating), chemical reduction, casting and dipping. Suitable vapor phase deposition methods include, for example, vapor deposition, metal plasma deposition, ion beam deposition, sputtering, magnetron sputtering, and other similar approaches. Vapor phase deposition techniques generally require varying degrees of vacuum, i.e., low pressure.

To effectuate electrochemical deposition, the biocompatible material must be rendered electrically conducting. Thus, if the material is not inherently electrically conducting, the material can be surface treated with graphite or the like to render the material electrically conducting. Electrochemical deposition involves the application of a voltage in order to electroplate elemental metal in contact with the biocompatible material. The polymer substrate with any required conductive coating functions as a cathode. The voltage required depends on the counter reaction and the concentrations of ions in solution. Selection of the metal composition in solution influences the effectiveness of the plating process. The electroplating generally is performed with an aqueous solution of a water soluble compound of the desired metal.

Chemical reduction is performed by placing the polymer substrate in a solution containing a salt of the desired metal. A chemical reducing agent is added to the solution to reduce the ionized metal to elemental metal in the presence of the substrate. For example, the substrate can be contacted with a solution including an antimicrobial metal composition. The metal compound generally is relatively soluble in the solvent being used. Suitable silver compounds include, for example, silver nitrate. Generally, the solution is relatively concentrated such that the process proceeds at a reasonable rate. A reducing agent is then added to the solution. The corresponding metal is then deposited upon reduction onto the substrate, as an elemental metal.

Suitable reducing agents include, for example, aldehydes, sodium borohydride, $H_2$, and CO for reduction of a variety of metals. Gaseous reducing agents can be bubbled through the solution. In particular, aldehydes are known to reduce silver ions to elemental silver. The traditional silver compound for the reduction with aldehydes is ammoniacal silver hydroxide $(Ag(NH_3)_2OH)$, "Tollen's reagent." Aldehydes can be supplied as partly unreacted multifunctional aldehyde compounds, such as crosslinking agents. Similarly, a palladium chloride solution can be reduced to form palladium metal using hydrogen or carbon monoxide (CO), which can be bubbled into the solution. Elemental copper can be precipitated from copper solutions by the addition of aluminum, iron or zinc particles.

Vapor phase deposition approaches can be relatively low temperature processes that can be performed with temperature-sensitive substrates. Vapor deposition generally involves the formation of a metal vapor at low pressure using a thermal or collision mechanism. Vapor deposition can simply involve directing vaporized metal toward the polymer substrate to be metalized.

Sputtering involves bombardment of a metal surface with ions of an inert gas. Collisions of the inert gas ions sputter or dislodge atoms and/or ions of the metal into the vapor state. Thus, sputtering is an alternative to thermal evaporation for obtaining atoms of the metal in the vapor state. Sputtering is an often used process for metal vapor deposition. The inert gas ions can be directed to the source metal surface with sufficient energy depending on the dissociation energy for displacing an atom from the metal source. If desired, sputtered atoms can be ionized by an electron beam or the like to produce metal ions that can be directed with electromagnetic fields toward the substrate.

Vapor deposition preferably is performed using ion-beam-assisted deposition (IBAD) under high vacuum as described, for example, in U.S. Pat. No. 5,474,797 to Sioshansi et al., incorporated herein by reference. IBAD involves an evaporator that forms a vapor of the desired metal. The metal vapor is delivered to the substrate with the assistance of a beam of ions formed from one or more gases.

For vapor phase deposition approaches, the substrate can be rotated to expose the different portions of the substrate to the metal vapor. If the substrate is rotated to uniformly expose the different portions of the substrate to the metal vapor, a uniform coating of metal is formed. Alternatively, a nonuniform coating can be formed by corresponding nonuniform exposure of the substrate surface to the metal vapor. Similarly, the composition of the metal vapor can be altered to produce a non-uniform metal composition over different portions of the substrate or within different layers along the substrate. Similarly, with solution/liquid based approaches, different portions can be exposed to the solution/liquid for the same or different periods of time to produce a non-uniform metal coating, by coating thickness and/or metal composition.

While the metal coating can be used to make relatively minor changes in the overall geometry of the component/device, the polymer substrate generally incorporates the major features of the ultimate composite. In particular, the metal can be applied nonuniformly with vapor phase or solution phase approaches to create deviations in the geometry of the resultant composite. These deviations, for example, can involve bulges, projections and the like, that can be produced by the application of additional metal at specific locations on the substrate.

Following deposition of the metal coating, the surface properties of the metal coating can be altered. In particular, the coating can be polished, etched, magnetized, oxidized, or otherwise modified to alter the surface characteristics.

Properties of the Metal/Polymer Composite

The resulting metal/polymer composite preferably includes a metal coating of sufficient thickness such that the resulting composite has desired levels of mechanical strength. The metal coating can result in improved mechanical properties. For most medical applications, the component generally has high fatigue endurance and low creep. Creep refers to permanent deformation with the passage of time as a result of the application of a load on the element. Thus, an element preferably does not significantly permanently deform with the passage of time. For heart valve stents, the stent component must be able to withstand 600 million cycles on an accelerated wear tester without failing and with low creep.

Biocompatible Materials

The medical devices of interest include at least a component comprising the metal/polymer composites described herein. The portions of the medical devices that are designed to contact the bodily fluids or tissues of a patient can include additional biocompatible materials, such as tissue, uncoated polymers, polymers with thin metal coatings, metal, and ceramics, within the same component as the metal/polymer composite or in separate components. These possible additional biocompatible materials are described in this section.

Appropriate biocompatible materials can be formed from natural materials, synthetic materials or combinations thereof. Natural, i.e., biological, material for use in the invention includes relatively intact living tissue, decellularized tissue and recellularized tissue. These tissues may be obtained from, for example, natural heart valves, portions of natural heart valves such as aortic roots, walls and leaflets, pericardial tissues, such as pericardial patches, connective tissues, bypass grafts, tendons, ligaments, skin patches, blood vessels, cartilage, dura mater, skin, bone, fascia, submucosa, umbilical tissues, and the like.

Natural tissues are derived from a selected animal species, typically mammalian, such as human, bovine, porcine, seal, equine, canine or kangaroo. These natural tissues generally include collagen-containing material. Natural tissue is typically, but not necessarily, soft tissue. Tissue materials are particularly useful for the formation of tissue heart valve prostheses. The tissue can be living tissue, decellularized tissue or recellularized tissue. Decellularization approaches are described, for example, in U.S. Pat. No. 5,855,620, incorporated herein by reference, and in published PCT Applications WO96/32905 and WO 96/03093, both incorporated herein by reference.

Tissues can be fixed by crosslinking. Fixation provides mechanical stabilization, for example, by preventing enzymatic degradation of the tissue. Glutaraldehyde or formaldehyde is typically used for fixation, but other fixatives can be used, such as other difunctional aldehydes, epoxides, and genipin and derivatives thereof. Tissues can be used in either crosslinked or uncrosslinked form, depending on the type of tissue, the use and other factors. Generally, if xenograft tissue is used, the tissue is crosslinked and/or decellularized.

Relevant synthetic materials include, for example, polymers and ceramics. Appropriate ceramics include, without limitation, hydroxyapatite, alumina and pyrolytic carbon. Ceramics can be coated with a polymer, protein or other compound prior to use as a substrate, if desired. Appropriate synthetic materials include hydrogels and other synthetic materials that cannot withstand severe dehydration. Biocompatible materials can be fabricated from synthetic polymers as well as purified biological polymers. Suitable synthetic polymers are described in the preceding section. These synthetic polymeric materials can be woven or knitted into a mesh to form a matrix or similar structure. Alternatively, the synthetic polymer materials can be molded or cast into appropriate forms.

Biological polymers can be naturally occurring or produced in vitro by fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelatin, polyamino acids, cat gut sutures, polysaccharides (e.g., cellulose and starch) and copolymers thereof.

Completion of the Medical Device, Storage, Packaging, Distribution and Use

The metal coated substrate can form an entire medical device itself, or the metal coated substrate can be incorporated with other biocompatible components into a medical device before or after formation of the coating. For example, a metal/polymer composite forming a heart valve stent can be incorporated into a tissue heart valve prosthesis, prior to storage and/or distribution of the resulting prosthesis. While in principle the coating can be performed following the formation of a multiple component medical device, the coating of a single component within the medical device generally would be performed prior to assembly of the components to avoid interference with the coating process by the other components.

The composite material can be stored appropriately prior to or following formation into a medical device. Generally, the composite would be stored in a dry, sterile environment. If components of the medical device require moisture to maintain their integrity, such as tissue components, the medical device with the metal/polymer composite can be stored in a moist, sterile environment. The moist environment can be maintained with or without immersing the medical device in a sterile liquid, such as aqueous glutaraldehyde.

For distribution, the medical devices are placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis and the like.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A medical device comprising a substrate having a biocompatible metal coating over at least a portion of its surface with an average thickness greater than about 3 microns, wherein the substrate comprises a polymer and wherein the amount of metal in the coating affects mechanical properties.

2. The implantable medical device of claim 1 wherein the metal coating has an average thickness greater than about 10 microns.

3. The implantable medical device of claim 1 wherein the metal coating has an average thickness from 10 microns to about 1000 microns.

4. The implantable medical device of claim 1 wherein the metal coating comprises an antimicrobial metal selected from the group consisting of silver, gold, platinum, palladium, iridium, copper, tin, lead, antimony, bismuth and zinc.

5. The implantable medical device of claim 1 wherein the metal coating comprises silver.

6. The implantable medical device of claim 1 wherein the metal coating comprises an anticalcific metal selected from the group consisting of aluminum, manganese and iron.

7. The implantable medical device of claim 1 wherein the metal coating comprises a metal selected from the group consisting of titanium, cobalt, stainless steel and nickel.

8. The implantable medical device of claim 1 wherein the metal coating comprises an alloy.

9. The implantable medical device of claim 1 wherein thickness of the metal coating at all points varies by less than about 10% relative to the average coating thickness.

10. The implantable medical device of claim 1 wherein the thickness of the coating at some point varies by a factor of ten or more relative to the average coating thickness.

11. The implantable medical device of claim 1 wherein thickness oL the metal coating at all points varies by less than from about 25% to about 250% relative to the average coating thickness.

12. The implantable medical device of claim 1 wherein the polymer substrate comprises a polymer selected from the group consisting of polyether ether ketones, acetals, polyamides, polyurethanes, polytetrafluoroethylene, polyester teraphthalate, polycarbonates, polysulfone, resorbable polymers, and copolymers and mixtures thereof.

13. The implantable medical device of claim 1 wherein the medical device is selected from the group consisting of a heart valve prosthesis, catheters, annuloplasty rings, heart valve stents, heart valve leaflets, vascular stents, urinary stents, mechanical heart components, pacemaker components, electrical leads, left ventricular assist devices, and orthopedic components.

14. A method of producing a medical device comprising applying a metal coating on a substrate, the metal coating having an average thickness greater than about 3 microns, wherein the substrate comprises a polymer and wherein the amount of metal in the coating affects mechanical properties.

15. The method of claim 14 wherein the coating process is performed by a vapor deposition method.

16. The method of claim 15 wherein the vapor deposition approach comprises ion-beam-assisted deposition.

17. The method of claim 15 wherein the vapor deposition approach comprises sputtering.

18. The method of claim 14 wherein the coating process is performed by electrochemical deposition, chemical reduction, casting, or dipping.

19. The method of claim 14 wherein the average thickness of the coating is greater than about 10 microns.

20. The method of claim 14 wherein the coating process is performed to achieve a nonuniform coating with different coating thicknesses over different portions of the substrate.

21. The method of claim 14 wherein the metal is selected from the group consisting of silver, gold, platinum, palladium, iridium, copper, tin, lead, antimony, bismuth, zinc, aluminum, manganese, iron, titanium, cobalt, stainless steel, nickel and alloys thereof.

* * * * *